United States Patent
Krause

(10) Patent No.: US 11,364,019 B1
(45) Date of Patent: Jun. 21, 2022

(54) CATHETER FOR LOWER LUNG FLUID SAMPLING

(71) Applicant: William R. Krause, Charlottesville, VA (US)

(72) Inventor: William R. Krause, Charlottesville, VA (US)

( * ) Notice: Subject to any disclaimer, the term of this patent is extended or adjusted under 35 U.S.C. 154(b) by 715 days.

(21) Appl. No.: 16/023,721

(22) Filed: Jun. 29, 2018

Related U.S. Application Data

(63) Continuation-in-part of application No. 14/209,852, filed on Mar. 13, 2014, now abandoned.

(60) Provisional application No. 61/785,516, filed on Mar. 14, 2013.

(51) Int. Cl.
  *A61B 10/00* (2006.01)
  *A61B 5/00* (2006.01)
  *A61B 17/34* (2006.01)

(52) U.S. Cl.
  CPC ........ *A61B 10/0051* (2013.01); *A61B 5/6853* (2013.01); *A61B 2017/3435* (2013.01)

(58) Field of Classification Search
  CPC .............. A61M 25/0119; A61M 16/04; A61M 25/006; A61M 25/008; A61M 25/0058–0059; A61M 25/0068; A61M 25/0074; A61M 25/00; A61M 25/10; A61B 2017/3435; A61B 10/02
  See application file for complete search history.

(56) References Cited

U.S. PATENT DOCUMENTS

| | | |
|---|---|---|
| 3,050,066 A | 1/1962 | Koehn |
| 3,168,092 A | 2/1965 | Silverman |
| 3,502,069 A | 3/1970 | Michael et al. |
| 3,713,447 A | 1/1973 | Adair |
| 3,734,094 A | 5/1973 | Calompg |
| 3,752,158 A | 8/1973 | Kariher |
| 3,766,927 A | 10/1973 | Jackson |
| 3,796,211 A | 3/1974 | Kohl |
| 3,800,781 A | 4/1974 | Zalucki |
| 3,830,225 A | 8/1974 | Shinnick |
| 3,856,020 A | 12/1974 | Kovac |

(Continued)

FOREIGN PATENT DOCUMENTS

GB 955490 4/1964

*Primary Examiner* — Devin B Henson
*Assistant Examiner* — H. Q. Nguyen
(74) *Attorney, Agent, or Firm* — Kimberly O Snead

(57) ABSTRACT

A catheter for introduction into a body cavity comprises a flexible outer tube with a handle member and proximal and distal ends and a flexible inner tube with a holder. The exterior surface of the outer tube has a first cross sectional shape along at least a portion of its length with the inferior surface having a second cross section shape along at feast a portion of its length. The inner tube has an exterior surface having a third cross section shape along at least a portion of its length. The third cross section shape has a radius less than said second cross section shape and is configured to prevent more than a predetermined rotation when received within in the second cross section shape of the outer tube. The holder has a holder stop proximate its distal face with the distance between the proximal face of the handle member and the stop being equal to the length of the membrane. This ensures that once the stop contacts the handle member, the membrane will be fully deployed.

20 Claims, 12 Drawing Sheets

(56) References Cited

U.S. PATENT DOCUMENTS

| | | |
|---|---|---|
| 3,867,945 A | 2/1975 | Long |
| 3,894,540 A | 7/1975 | Bonner, Jr. |
| 3,896,815 A | 7/1975 | Fettel et al. |
| 3,938,530 A | 2/1976 | Santomieri |
| 3,941,119 A | 3/1976 | Corrales |
| 3,952,747 A | 4/1976 | Kimmell, Jr. |
| 3,981,299 A | 9/1976 | Murray |
| 3,982,544 A | 9/1976 | Dyck |
| 3,985,139 A | 10/1976 | Penar |
| 3,989,571 A | 11/1976 | Harautuneian |
| 3,993,080 A | 11/1976 | Loseff |
| 4,018,231 A | 4/1977 | Wallace |
| 4,023,559 A | 5/1977 | Gaskill |
| 4,029,104 A | 6/1977 | Kerber |
| 4,038,519 A | 7/1977 | Foucras |
| 4,243,040 A | 1/1981 | Fogarty et al. |
| 4,318,410 A | 3/1982 | Chin |
| 4,321,915 A | 3/1982 | Leighton et al. |
| 4,324,262 A | 4/1982 | Hall |
| 4,413,633 A | 11/1983 | Yanda |
| 4,437,857 A | 3/1984 | Goldstein |
| 4,476,866 A | 10/1984 | Chin |
| 4,497,324 A | 2/1985 | Sullivan et al. |
| 4,530,698 A | 7/1985 | Goldstein et al. |
| 4,604,094 A | 8/1986 | Shook |
| 4,606,347 A | 8/1986 | Fogarty et al. |
| 4,641,654 A | 2/1987 | Samson et al. |
| 1,862,381 A | 5/1987 | Inaba |
| 4,753,223 A | 6/1988 | Bremer |
| 4,762,133 A | 8/1988 | Bayne et al. |
| 4,771,765 A | 9/1988 | Choy et al. |
| 4,776,841 A | 10/1988 | Catalano |
| 4,785,795 A | 11/1988 | Singh |
| 4,785,806 A | 11/1988 | Deckelbaum |
| 4,785,815 A | 11/1988 | Cohen |
| 4,815,478 A | 3/1989 | Buchbinder et al. |
| 4,946,440 A | 8/1990 | Hall |
| 5,507,766 A * | 4/1996 | Kugo ................ A61M 25/0053 606/194 |
| 8,827,951 B2 * | 9/2014 | Besser ............. A61B 17/22032 604/97.02 |
| 9,737,671 B2 * | 8/2017 | Williams ........... A61B 17/3474 |
| 2011/0201887 A1 | 4/2011 | Greenblatt |

* cited by examiner

Figure 1A
Figure 1B
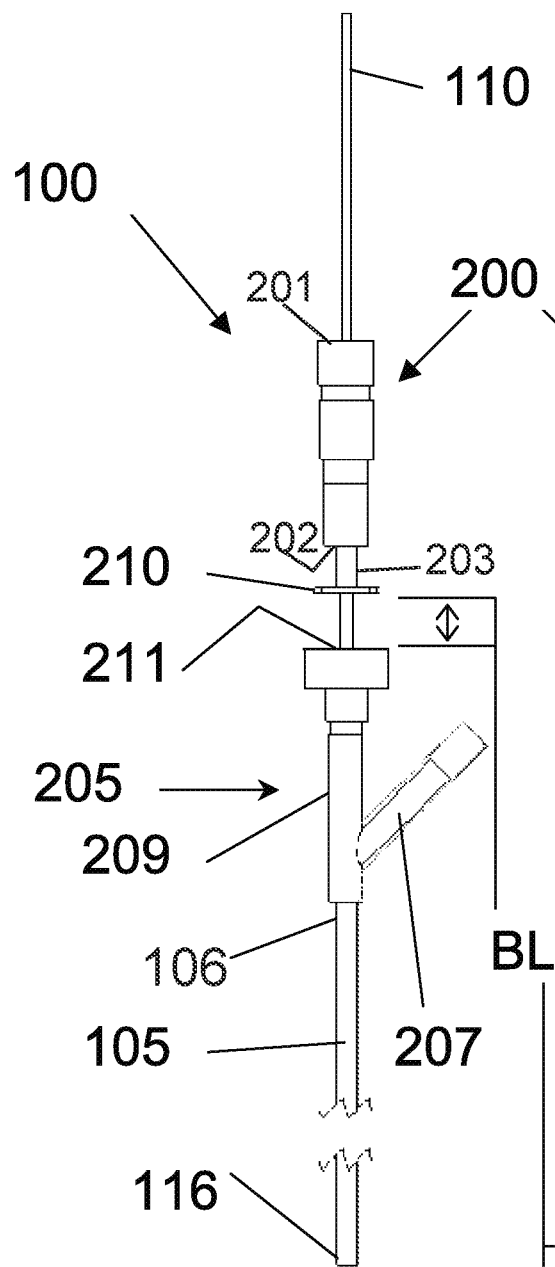
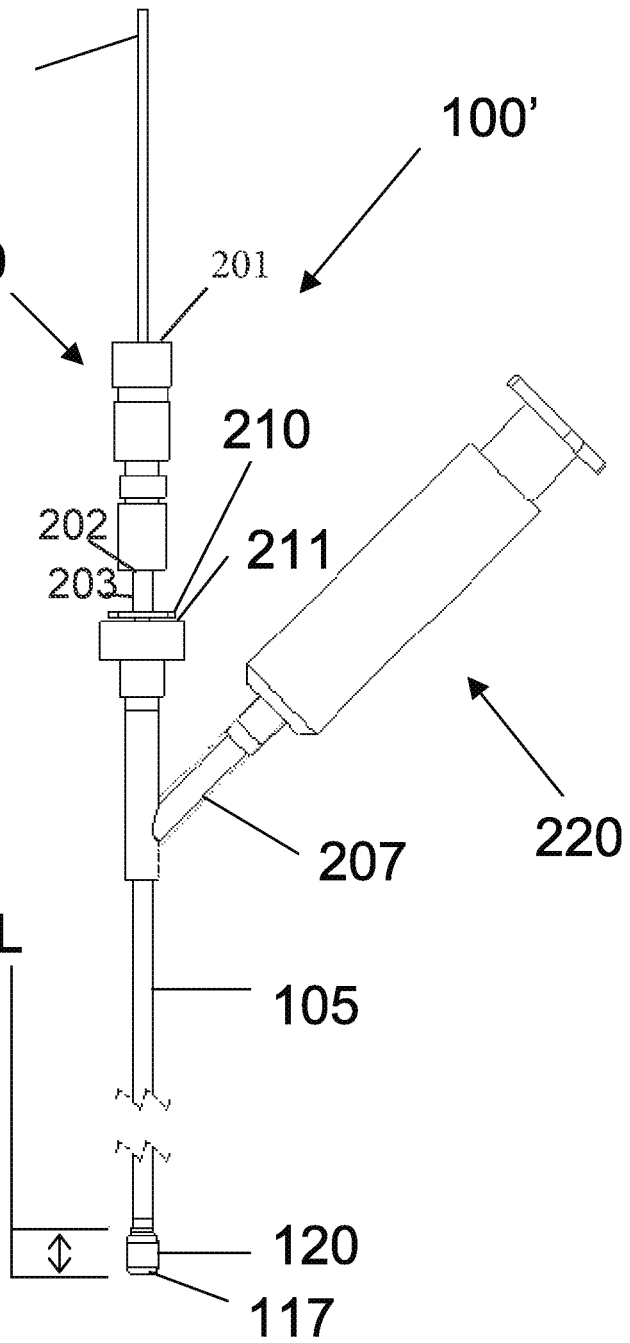

CATHETER FOR LOWER LUNG FLUID SAMPLING

FIELD OF THE INVENTION

The present invention the invention relates to a disposable diagnostic catheter system, more particularly a catheter configuration that prevents rotation between catheters as well as a limiting mechanism to enable proper balloon deployment.

BACKGROUND OF INVENTION

For certain groups of medical patients who are in the intensive care unit on ventilator assistance, common infections, such as pneumonia, carry a high mortality rate. Successful treatment of bacterial infections in the lower pulmonary tree is facile when the responsible pathogen is properly identified enabling the patient to be treated with a narrow spectrum antibiotic specific to the invading bacteria. Traditionally, the diagnosis of nosocomial pneumonia has been performed by a cytological examination of the sputum from the patient. The results of the sputum sample would show numerous potential pathogens, the majority of which do not contribute to the life-threatening infection. The contaminating organisms originate from bacteria colonizing in the oropharynx and around the endotracheal tube, while the culpable pathogen infects the bronchioles and alveoli of the lower respiratory track. It is arduous, and frequently inaccurate, to differentiate between the infecting and colonizing bacteria in the sputum sample. The sampling method, and therefore patient care, would be greatly improved if the lower airway track could be accessed and an uncontaminated fluid sample obtained. Bronchoscopy arose to fill this need, using fiber optic cables to visualize the pulmonary tree and separate lumens to collect samples from the terminal bronchioles.

Sampling instruments that transverse the lumens can be separated into two sampling techniques: protected specimen brushing and bronchoalveolar lavage. An advantage of using a bronchoscope in conjunction with bronchoalveolar sampling is the "wedging" that occurs when the distal tip of the bronchoscope reaches the bronchiole section with the same outer diameter as the scope. This keeps secretions from the trachea and upper airways from dripping down the endoscope and contaminating the sampling region.

There are, however, several major drawbacks to bronchoscopic diagnosis of bacteriological infections of the lower pulmonary track. Primarily, the sampling lumen of the bronchoscope is unprotected at the distal opening and becomes contaminated as the scope is guided down the pulmonary track. When the sampling apparatus is passed through the sampling lumen, it is exposed to these impurities before it reaches the target region. A microbiological analysis then shows both the responsible pathogen and the contaminating upper airway bacteria, which are unrelated to the condition of the patient's lung. Since the physician cannot tell which bacterium is causing the illness, they must prescribe a broadspectrum antibiotic that does not always completely eliminate the culpable pathogen.

Another disadvantage involves the act of "wedging" a rigid bronchoscope into the fragile bronchioles and alveoli. Damage to the lower pulmonary track can occur at minimal forces and complicate the treatment of the patient. Another issue with bronchoscopy is the economic impact on smaller hospitals or institutions without substantial funding. The endoscopic equipment is expensive to purchase and requires extensive sterilization procedures. After a single use, the endoscope undergoes extensive cleaning, disinfecting and sterilization procedures that must be meticulously performed. The sterilization process is difficult because of the equipment's low tolerance to heat, chemicals, and trauma. Specially trained personnel are needed to handle and correctly execute the sterilization process of the bronchoscopes, which generally take 24 hours to complete. This means that only one endoscopic procedure can be performed with a single bronchoscope each day, causing busier hospitals to purchase and maintain several endoscopes at all times.

To overcome the limitations of bronchoscopic sampling, a multitude of diverse "blind" bronchial sampling devices have been developed to conduct non-bronchoscopic sampling of the lower airways. In the blind bronchial sampling, a flexible catheter is introduced into the trachea and transverses the pulmonary tree until it reaches the lower bronchioles. Radio opaque stripes are used to mark the length of the catheter, which allows the placement catheter tip to be visualized in real-time using fluoroscopic, X-ray techniques or other imaging technologies. The equipment required is expensive and can be limited to larger medical institutions. Some blind bronchial sampling catheters, such as U.S. Pat. No. 4,981,477, have specialized tips that are fashioned in a manner that allows the user to access to either lung by rotating the device. In general use, however, neither lung is pre-selected as the target area and the sampling region is the lower airway.

The aforementioned diagnostic instruments use either bronchoalveolar lavage or protected specimen brush as the sampling technique, both of which can be implemented at the patient's bedside. Samples of fluid or tissue are routinely taken from patients for analysis to diagnose an affliction. Although significant research has attempted to determine the superior sampling technique, neither has been found to be vastly superior. In one method of use, the present catheter system uses a cytological specimen brush as the sampling device. In another embodiment, a lavage-aspiration sample collection method replaces the specimen brush.

Protected specimen brushing is one sampling method comprised of passing a cytology brush through the pristine lumen of the inner catheter to the target area. The brush is advanced slightly past the distal tip of the inner catheter and rubs against tissue to scrape off cells and lodge them into the bristles. The brush is then removed and the cellular material is collected in a sterile solution and analyzed for its microbiological content. This sampling method is described in U.S. Pat. Nos. 4,763,670 and 5,792,074 where the sampling brush is maintained in an uncontaminated environment by sealing the end of the catheter with a watersoluble plug.

A representative sample of the infecting bacteria can also be made using bronchoalveolar lavage. This technique is increasingly used to diagnosis infections and other abnormalities of the alveoli at the terminus bronchioles of a medical patient. U.S. Pat. Nos. 5,158,569, 5,246,012, and 5,297,560 describe a bronchoalveolar lavage catheter and method of using thereof. In bronchoalveolar lavage, commonly referred to as BAL, aliquots of sterile fluid are infused into the lower pulmonary tree then aspirated back into a sterile collection device to be cultured and analyzed for pathogens flushed from the inside of the alveoli. For the described devices, pathogens from the upper airway can be transported down to the lower airway on the tip and outer surface of the device and get deposited and subsequently falsely sampled as representative of the lower airway.

U.S. Pat. Nos. 4,324,262 and 4,946,440 describe a catheter having an outer and inner tube with a cylindrical membrane connecting the distal ends of the two tubes. After the inner tube is extended, a fluid may be introduced into an annular space between the tubes to inflate the membrane. A significant disadvantage of this device is that the inner tube is free to rotate relative the outer tube thus twisting the membrane. With the membrane twisted, it can be difficult or at times impossible to extend the inner tube. If extended in the twisted position, typically the membrane closes off the distal opening to the enclosed pristine chamber of the inner tube. In addition, the twisted membrane prevents the inserted fluid from expanding the membrane as intended. With the distal end of the catheter inserted into the body the operator cannot see if the tubes are twisted thus may not be able to extend the inner tube and expand the membrane. If the inner tube does not extend then the operator must remove the catheter and retry.

SUMMARY OF THE INVENTION

One purpose of the present invention is to improve the accuracy of diagnostic techniques for infections and other abnormalities of the lungs. The primary advantage of the present invention is to provide a means to prevent the inner tube from rotating or twisting relative to the outer tube and causing the attached membrane to not expand when inflated. Another is to perform the diagnosis procedure without the accompaniment of a visualization device such as a bronchoscope. The invention allows multiple samples to be made during one procedure by maintaining the uncorrupted environment of the sampling region distal to the inflated balloon.

The disclosed disposable catheter system for introduction into a body cavity comprises a flexible outer tube with a handle member and proximal and distal ends and flexible inner tube with a holder. The flexible inner tube is slidable with respect to the outer tube and defines an annular space there between. A membrane, having a predetermined length, is coupled to the distal end of the outer tube and the distal end of the inner tube.

A diagnostic catheter system for introduction into a body cavity has a handle with proximal and distal faces, a handle stop adjacent the distal face; and a receiving area extends from the proximal face to the handle stop. The receiving area is dimensioned to receive and secure a flexible inner tube. A Y connector has a proximal and distal face with a tube receiving area there between and a port for introducing a fluid under pressure into an annular space created by the flexible inner tube and an outer tube to permit a fluid transfer volume of about 1.5 cu. mm per 1 mm length.

The flexible outer tube has an exterior periphery having a first cross sectional configuration and a first dimension; an interior periphery having at least one second cross sectional configuration and a second dimension less than the first dimension. The distal end is adapted for insertion into a body cavity and the proximal end is connected to the distal face of the Y connector. The outer diameter of the outer tube is about 4 mm.

The flexible inner tube which is dimensioned to be received within the handle receiving area has an exterior periphery having at least one third cross sectional configuration and a third dimension less than the second dimension and an interior periphery having a fourth cross sectional configuration and a fourth dimension less than the third dimension. The outer diameter of the flexible inner catheter is about 1.5 mm to 2 mm.

The second dimension of the outer tube and third dimension of the inner tube form the annular space that enables a fluid transfer volume to inflate a membrane coupled to the distal end of the flexible outer tube and the distal end of the flexible inner tube. The third cross sectional shape and the second cross sectional shape are configured to prevent more than a predetermined rotation and to provide a predetermined flex and are generally the same polygon. The second cross sectional shape and third cross section shape can extend the length of the catheters or only at the distal end.

When the handle is in a retracted position the handle stop is distanced from the proximal face of the Y connector a distance equal to the everted length of the membrane, between 5 mm and 10 mm. When the handle is in a deployed position the handle stop contacts the proximal face of the Y connector to prevent insertion of the flexible inner tube into the flexible outer tube beyond the everted length of the membrane, the distance between the retracted position and deployed position being balloon deployment.

BRIEF DESCRIPTION OF THE DRAWINGS

These and other objects, features, advantages and aspects of the present invention can be better understood with reference to the following detailed description of the preferred embodiments when read in conjunction with the appended drawing figures.

FIG. 1A is a side view of the catheter in accordance with the disclosed invention;

FIG. 1B is a side view of the catheter with the syringe mounted and the balloon extending from the distal tip in accordance with the disclosed invention;

DETAILED DESCRIPTION OF THE INVENTION

Definitions

Figure 2:
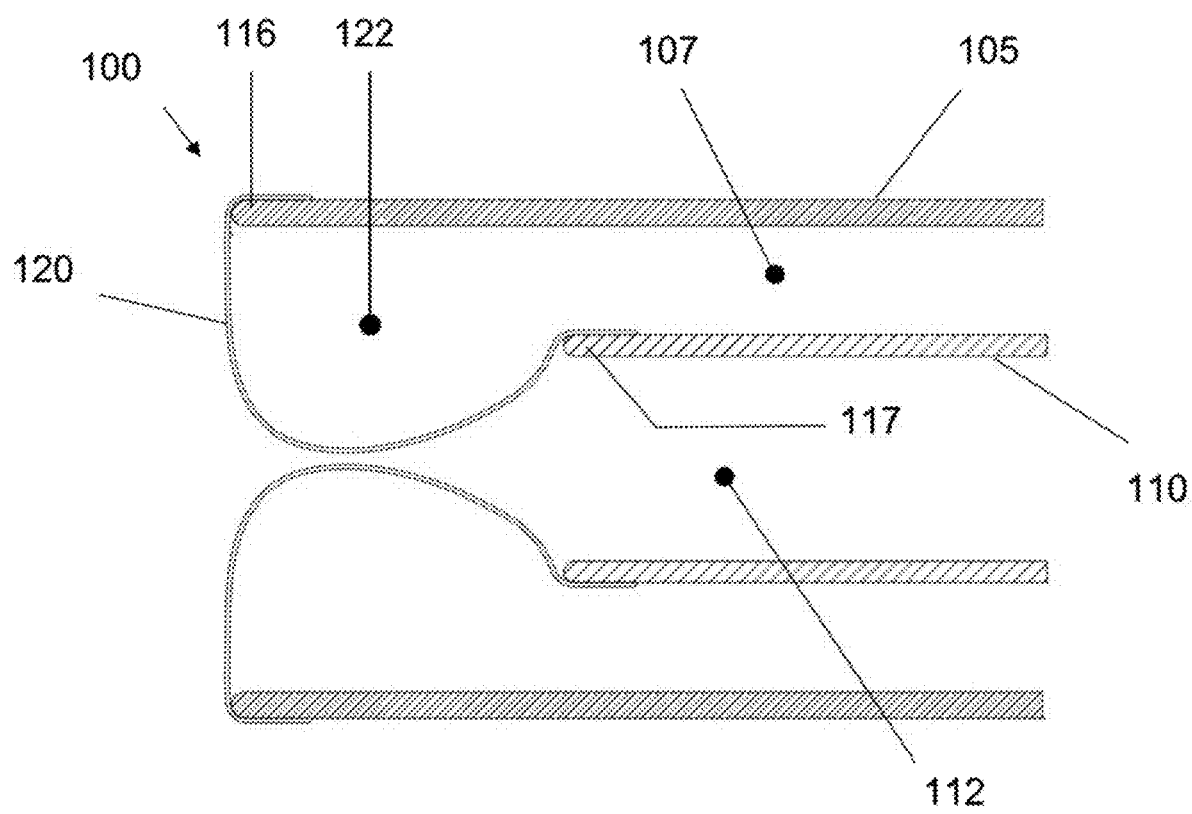
FIG. 2 is a cutaway view of the distal tip of the catheter showing the balloon in the retracted position in accordance with the disclosed invention.

As used herein the term "about" refers to a variation of +/−15%.

As used herein the term "fluid transfer volume" refers to the amount of fluid transferred by the displacement of the plunger in the syringe connected to the holder.

As used herein the term "balloon deployment" is act of moving the handle stop to contact the proximal face of the Y connector and thereby everting the balloon.

The disclosed catheter system prevents rotation between the inner and outer tubes while providing a fluid transfer volume, upon balloon deployment, to fully evert a flexible membrane. A holder stop is spaced from the proximal end of the Y connector to ensure that the balloon, or membrane, is fully deployed without over deployment to cause tearing. The inner catheter tube 110 and outer catheter tube 105 are dimensioned, as described hereinafter, to enable sufficient fluid transfer volume to inflate the balloon upon compression of the handle, or balloon deployment, bringing the holder stop in contact with the proximal end of the Y connector.

FIG. 1A shows a catheter device, 100, in its retracted state. The device 100 consists of a "Y" connector 205 connected to the proximal end 106 of an outer catheter 105. The Y connector 205 has a side arm 207 for attachment of a standard inflation syringe 220 (FIG. 1B) and a proximal port 209 to receive the inner catheter 110. The inner catheter 110, which is dimensioned to be slidable within the outer catheter 105, is inserted through the proximal port 209, through the Y connector 205 and through outer catheter 105. Attached to the inner catheter 110 and the outer catheter 105 at the distal end 116 is a flexible membrane 120, as shown in FIG. 1B, that is recessed in the distal end 116 of the outer catheter 105. In the retracted position, as received from the manufacturer, FIG. 1A, the inner catheter holder 200, having a proximal face 201, distal face 202 and handle receiving area 203, places the inner catheter 110 in the correct orientation at a predetermined fluid transfer volume, indicated as BL The predetermined distance BL is the distance, between 5 mm and 10 mm, required to evert the balloon can be seen by the holder stop 210 distance BL (FIG. 1A) from the proximal face 211 of the Y connector 205 that is equal to the balloon 120 deployment distance BL (FIG. 1B). The inner catheter 110 is then inserted until the specialized holder stop 210 at the base of the holder 200 is adjacent to the proximal face 211 of the Y connector 205. FIG. 1B shows the device 100 with the distal balloon 120 extended from the distal tip 116 of the outer catheter 105. The inflation syringe 220 is sized in accordance with the prior art and in FIG. 1B is shown with the plunger in the retracted position. The inflation syringe 220 inflates the balloon, or membrane, 120 to form a seal to prevent contaminants from entering the lower airway. It should be noted that balloon and membrane will be used interchangeably herein. FIGS. 1A and 1B show the device in both the retracted and deployed configuration, respectively, to illustrate the connection between the distance BL, the specialized holder stop 210 movement and the length of the balloon 120. When the device 100 is in place and ready for balloon 120 deployment, the user advances the inner catheter 110 relative to the outer catheter 105 until the holder stop 210 reaches the proximal face 211 of the Y connector 205. This displacement everts the balloon 120 to its full length, BL. Once the balloon 120 is everted, the inflation syringe 220 is attached to the Y connector 205 and fluid (air) is introduced to inflate the balloon 120 which has a fluid capacity of 100 to 1000 cubic millimeters. Without the use of the holder stop 210, the user would be unable to determine whether the balloon 120 has been extended to the desired extension and ready for deployment. If the balloon 120 is not fully deployed, it everts within the outer catheter 105, thereby blocking the outer catheter 105 and preventing the gathering of a specimen. If the inner catheter extends too far beyond the outer catheter, the balloon could potentially be stretched too far and ripped.

It is at the point of insertion of the inner catheter 110 that the potential for twisting first arises. As the inner catheter 110 is inserted through the narrow passage of the holder 200, Y connector 205 and into the outer catheter 105, the inner catheter 110 can be twisted. As stated heretofore, a significant disadvantage of prior art devices is that the inner tube is free to rotate relative the outer tube thus twisting the membrane. With the membrane twisted, it can be difficult, or at times impossible, to extend the inner tube. If extended in the twisted position, typically the membrane closes off the distal opening to the enclosed pristine chamber of the inner tube. In addition, the twisted membrane prevents the inserted fluid from expanding the membrane as intended. With the distal end of the catheter inserted into the body the operator cannot see if the tubes are twisted thus may not be able to extend the inner tube and expand the membrane. If the inner tube does not extend then the operator must remove the catheter and retry.

FIG. 1B shows the side view of the device 100 with a broken section along the continuous portion of the inner catheter 110 and outer catheter 105. The device 100 is in the deployed position with the balloon 120 fully everted and inflated. The deployed position is achieved by advancing the inner catheter 110 relative to the outer catheter 105. The distance the inner catheter 110 can advance is limited by the specialized holder stop 210, at the base of the holder 200, and reaches maximum deployed distance BL when the holder stop 210 reaches the proximal end 211 of Y-connector 205. This distance is pre-determined and is equal to the length of the fully deployed balloon 120. Once the balloon 120 is fully deployed, gasket 204 (FIG. 7) inside Y-connector 205 is closed to seal the interior channel 107 between the outer catheter 105 and the inner catheter 110 from the atmosphere. The balloon 120 is then inflated by introducing fluid from the syringe 220. FIG. 2 shows the partial longitudinal cross-section of the distal end of the device, 100, in the retracted position. The inner catheter 110 terminates slightly proximal to the outer catheter 105 in the retracted position. The balloon membrane 120 is bonded to one surface of the outer catheter 105 and also on the surface of the inner catheter 105 as illustrated in FIG. 2. The balloon membrane 120 which is comprised of a high-volume, low-pressure material, folds into the space between the tips of the outer catheter 105 and inner catheter 110. This folded position of the balloon material 120 prevents biological contamination from entering the space 112 inside the inner catheter 110.

The balloon inflation space 122, is at the end of the inner catheter 110, and the outer catheter 105. This inflation space 122 is in communication, via channel 107 between the inner catheter 110 and the outer catheter 105, with the inflation syringe 220 at the proximal end of the device 100. When the inner catheter 110 is extended past the distal tip 116 of catheter 105, fluid (air) is injected into channel 107 to fill the space 122 and inflate the balloon 120. Preferably the inner walls of the balloon material 120 come in contact with one another to completely seal the inner space 112 from the external environment (FIG. 2 shows a slight gap only for illustrative purposes).

Figure 3:
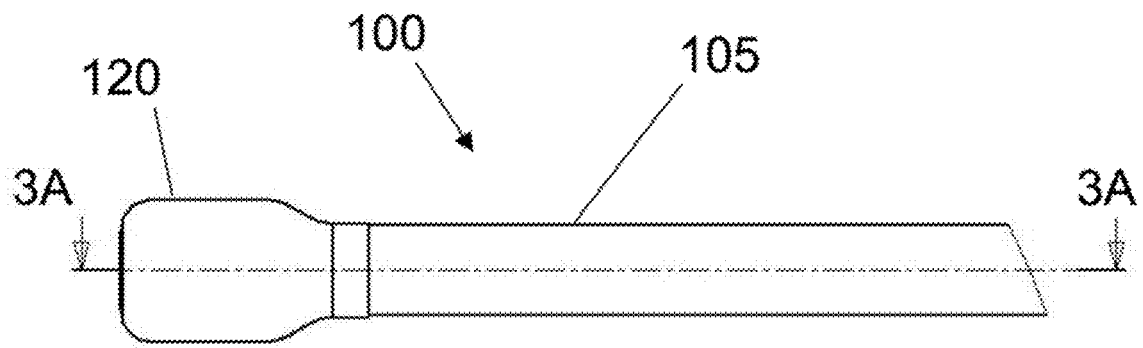
FIG. 3 is a fragmentary side view of the distal tip of the catheter in the deployed position wherein the balloon is everted and inflated in accordance with the disclosed invention.

FIG. 3 shows the distal tip of the device 100 in the deployed position wherein the balloon 120, is everted and inflated. The cross sectional line 3A transverses the longitudinal axis of the device 100, and the cross section view is displayed in FIG. 4.

Figure 4:
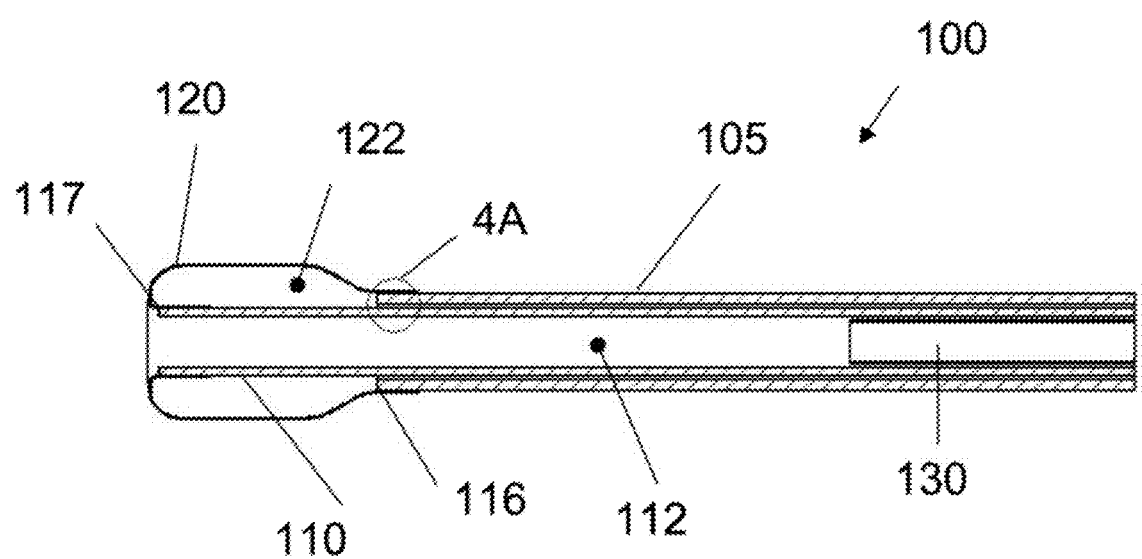
FIG. 4 is a cross-sectional view of the interior of the distal tip of the catheter designated by the line 3A described in FIG. 3.
Figure 5:
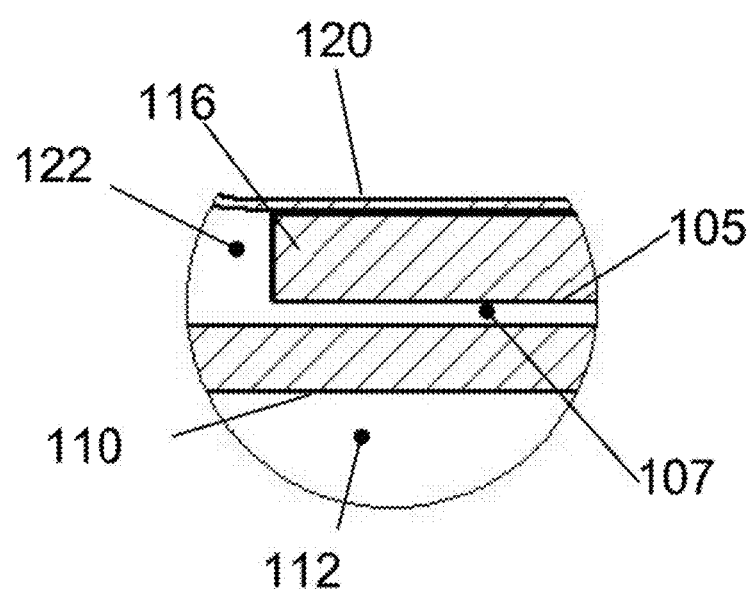
FIG. 5A is an enlarged detail view showing the continuous balloon space that extends beyond the outer catheter, external to the inner catheter, and connects with the inner space.
FIG. 5B is an enlarged detail view illustrating the corresponding cross sections of the inner and outer catheters in accordance with the invention.

FIG. 4 is the cross-sectional view of the interior of the device 100 designated by the line 3A described in FIG. 3. The device 100 is shown in the deployed position with the balloon 120 everted. To evert the balloon material 120 the inner catheter 110 is moved from the proximal end of the device 100 within the outer catheter 105. As the balloon material 120 is bonded to the surfaces of both the inner catheter 110 and the outer catheter 105, a seal is formed that enables inflation. The figure shows the balloon 120 bonded to the outer surfaces of the inner 110 and outer 105 catheters for convenience in manufacturing, although any configuration can be used that will enable the balloon to be easily everted while maintaining the sealed environment. Advancement of the inner catheter 110, in this example a hexagon, beyond the outer catheter 105 forces the balloon material 120 to evert into the desired position. The balloon space 122, is filled with fluid that gently expands the high-volume, low-pressure balloon membrane 120. Slightly proximal from the distal tip 117 of the inner catheter 110 and distal tip 116 of the outer catheter 105 is the sampling catheter 130 which resides within the interior space 112 of the inner catheter 110. The sampling catheter 130 can be any applicable method of obtaining microbiological samples from tissues. The sampling catheter 130 remains proximal to the balloon 120 until the balloon space 122 is fully inflated, the catheter 130 is then advanced by the user from the proximal end of the device 100 past the distal tips 116 and 117 of the outer catheter 105 and the inner catheter 110, respectively to contact the target sampling region. The area 4A is a view shown in FIG. 5 illustrating in detail the balloon space 122 as it exists between the inner catheter 110 and the outer catheter 105.

FIG. 5A is an enlarged detail view from the section designated by section 4A in FIG. 4. This shows the continuous balloon space 122 that extends beyond the outer catheter 105 and external to the inner catheter 110 and connects with the inner space 107 extending the length of the device 100. When fluid is introduced by the user from the connected syringe 220 proximal end of the device 100, FIG. 1B, it travels in the space 107 between the inner catheter 110 and outer catheter 105 and inflates the balloon 120. The balloon 120 is bonded to the surface of the outer catheter 105 as well as the surface of the inner catheter, 110. The high-volume, low-pressure material of balloon 120 inflates with increased amounts of fluid and seals off the target area from contamination on the outer surface of the catheter 105.

Independent from the balloon inflation space 122 is the interior space 112 of the inner catheter 110 that remains sterile as the sampling device 130 is being introduced into the target area.

Figure 5B:
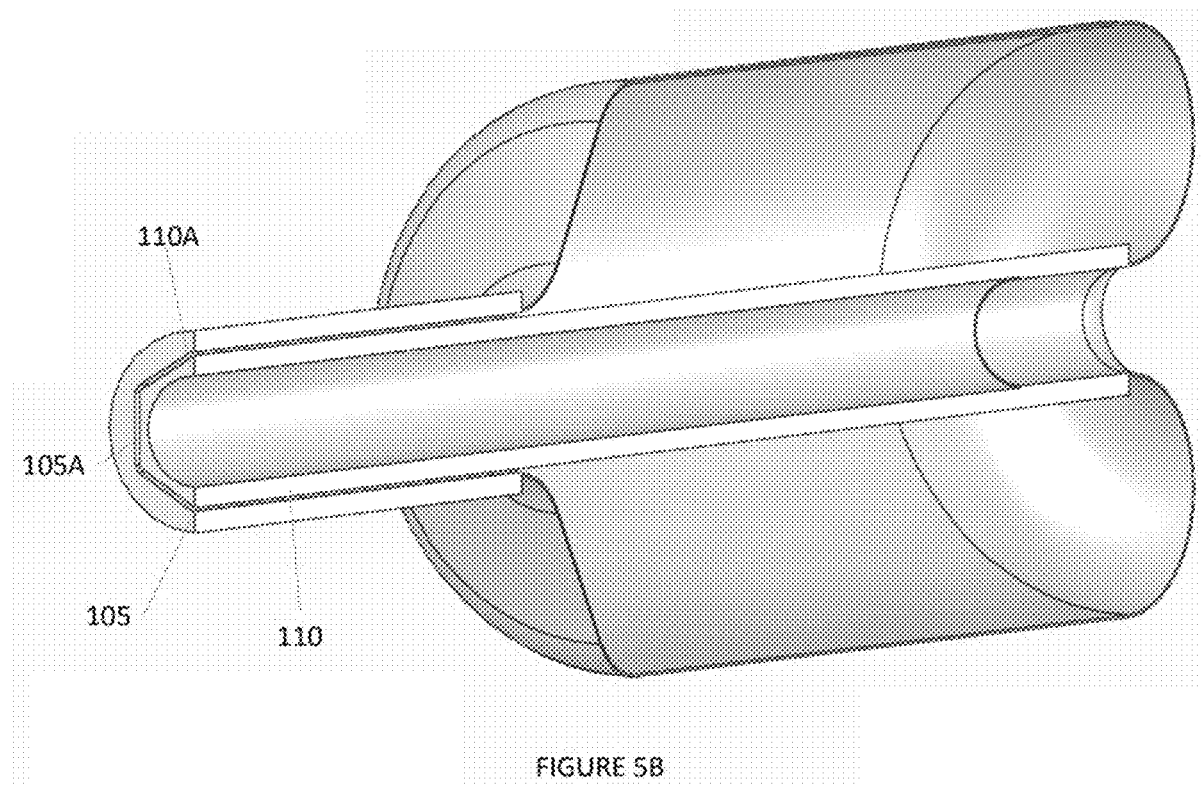

As can be seen in FIG. 5B, the edge 110A of the inner catheter 110 as an outer cross section that is complimentary to the inner cross section 105A of the outer catheter 105. In this figure, the outer cross section of the inner catheter 110 and inner cross section of the outer catheter 105 have a hexagonal shape. This is only one combination that can be used to prevent the inner catheter 110 from rotating within the outer catheter 105. In order to insure the balloon will inflate and to preserve the balloon and prevent tearing of the material, the inner and outer catheters need to remain in alignment and resist twisting relative to one another. FIGS. 6A through 6G show several, although not inclusive, examples of designs for the axial cross-section of the catheter. Shown are the cross sections of the inner catheters 110A-G and the outer catheters 105A-G that depict the interior space of the inner catheters 112A-G as well as the inflation spaces 107A-G. The non-rotating design can run either the entire or partial length of the catheter. If the non-rotating design runs only through a portion of the catheter, the distal end of the catheter is most critical. For maximum results the rotation between the outer cross section of the inner catheter 107 A-G and inner cross section of the outer catheter 105 A-G, should be less than about 15 degrees, although results will be achieved with a rotation up to 45 degrees.

Although a number of potential designs are illustrated, the optimal configuration is illustrated in FIGS. 6A, 6C, 6E and 6F. These configurations will provide the optimal flex modulus, or flexibility to rigidity combination, and will be most cost effective. Other designs, however can be incorporated depending upon end use. The flex modulus is critical in that, unlike may prior art designs, guide wires are not used and the maneuverability of the catheter is reliant on the configuration of the catheters.

The center 112 A-G of all illustrated catheters is circular for convenience as the sampling brushes are circular. This is the most economical design however it should not be considered a limitation as other designs can be used.

Figures 6A, 6B, 6C:
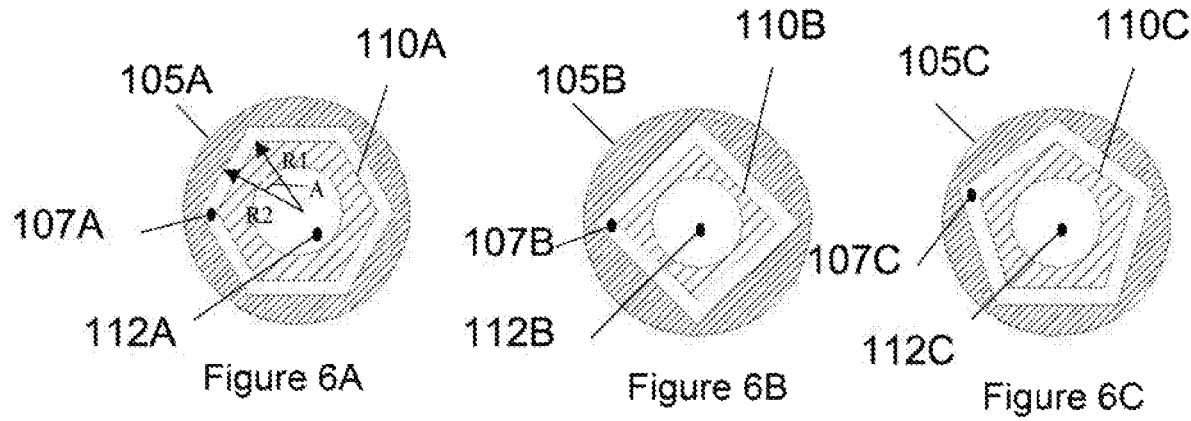
FIG. 6A is an axial cross section of one embodiment of the catheter in accordance with the invention.
FIG. 6B is an axial cross section of another embodiment of the catheter in accordance with the invention.
FIG. 6C is an axial cross section of an embodiment of the catheter in accordance with the invention.
Figures 6D, 6E, 6F:
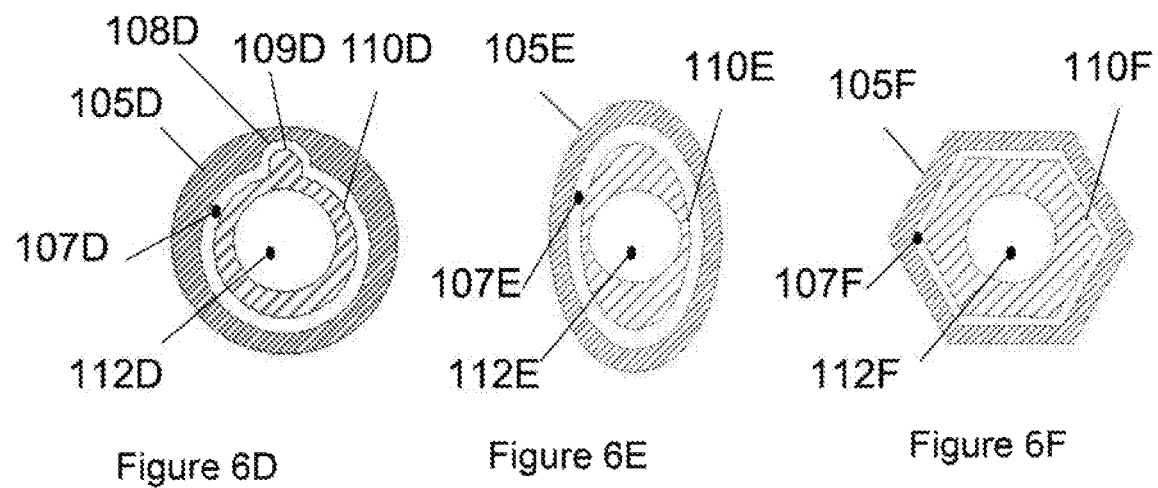
FIG. 6D is an axial cross section of another embodiment of the catheter in accordance with the invention.
FIG. 6E is an axial cross section of an additional embodiment of the catheter in accordance with the invention.
FIG. 6F is an axial cross section of another embodiment of the catheter in accordance with the invention.
Figure 6G:
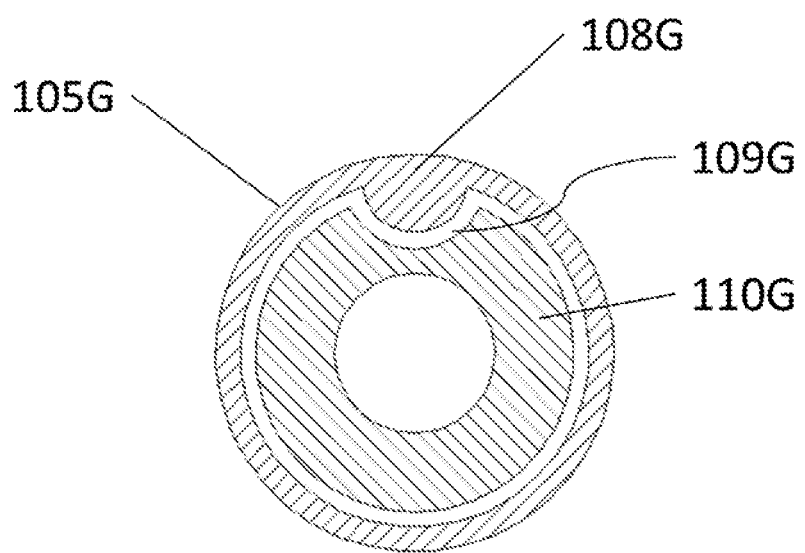
FIG. 6G is an axial cross section of another embodiment of the catheter in accordance with the invention.

For FIGS. 6A, 6B, and 6C, the exterior of the outer catheters 110 A-C are circular, however, the interior is shaped like a polygon with the intervening spaces 107A-C dimensioned to prevent the inner catheters 110A-C from rotating relative to the outer catheters 105A-C while still enabling the required fluid transfer volume. The exterior of the inner catheters 110AC is the same polygon shape as the interior of the outer catheter 105A-G only slightly smaller to allow the inner catheters 110A-C to nest within the outer catheters 105A-C. The interior of the inner catheter 110A-C and the exterior of the outer catheter 105A-C can be circular in the configurations presented in FIGS. 6A, 6B, and 6C or any other desired shape. FIG. 6D shows the two catheters, outer catheter 105D and inner catheter 110D in a mostly circular aspect with a notch 108D along the length, or a significant portion of the interior of the outer catheter 105D. Nesting within the notch 108D is a complementary protrusion 109D on the exterior of the inner catheter 110D. The notch 108D and protrusion 109D resist twisting and prevent the two catheters 105D and 110D from rotating relative to each other. The reverse of this is illustrated in FIG. 6G wherein the outer catheter 105G contains the protrusion 108G with the notch 109G being within the inner catheter 110G. The configuration may have multiple notches and protrusions along the circumference of the catheters. Further the notch, or notches, can be located in the inner catheter while the protrusion, or protrusions, are located in the outer catheter. Another configuration to maintain proper alignment is presented in FIGS. 6E and 6F. The outer catheters 105E and F, and inner catheters 110E and F, are identical, non-circular shapes with the inner catheters 110E and F, being smaller than the outer catheters 105E and F, however large enough to nest and prevent free rotation.

In FIG. 6A the exterior of the outer catheter 105A is circular with a hexagon interior.

The exterior of the inner catheter 110A is a hexagon with a circular interior 112A. To better describe the dimensioning of the catheters of this figure, the angle of the hexagon is illustrated by arrows R1 and R2. The apex of the angle A is in the center of the interior 112A with R1 extending to the exterior of the inner catheter 110A and R2 extending to the inner surface of the exterior catheter 105A, at the midpoint between angles. The space 107A between the two catheters 105A and 110A provides the fluid passage. The angle A created by R1 and R2 is about 10° to 15° and R1 has a length of about 2 mm. Although not illustrated in detail in all figures, the same dimensions apply to all Figures.

Although the inner catheters 110A-G must not rotate within the outer catheter 105A-G, it is critical that the space 107A-G between the two catheters be dimensioned to permit sufficient fluid passage while preventing rotation. As stated heretofore, the balloon 120 has a maximum safe volume of 0.1 to 0.2 cubic inches. This volume must be achieved by the fluid transfer volume during the depression of the handle 200, causing the stop 210 to come in contact with the proximal face 211 of the Y connector 205. The preferred distance between the stop 210 and the proximal face 211 should be no more than 10 mm and no less than 5 mm. In order to evert the balloon 120 the fluid transfer volume required must be completed within the above distance. In all designs, the volume of space 107A-G between the interior of the exterior catheter 105A-105G and the outer dimension of the interior catheter 110A-G must have a volume of about 1.5 cubic mm ($6.1 \times 10^{-5}$ cu in) per 1 mm of catheter length (0.04 in).

The device 200 is most commonly used in lower bronchi sampling and the catheter must, therefore, be able have the ability to harmlessly transverse tissues while still being guidable. The prior art bronchial catheter has an outer diameter range of 3 to 6 mm (HALYARD* Mini-BAL Sampling Catheter, Halyard Health Global, Alpharetta, Ga. 30004) and is a single hollow tube with a thickness sufficient to provide the required rigidity. Thinner catheters are often used with the addition of a guidewire to provide control.

The addition of an inner tube requires critical re-dimensioning. The OD of the outer catheter 105A-G cannot simply be expanded to accommodate a standard sized inner catheter 110A-G while still remaining comfortable for the patient. Therefore, while the OD is increased slightly the thickness of the walls of the catheters are reduced. To compensate for the thinning of the catheter walls, the rigidity is increased through the configuration of the catheters.

Although any of the illustrated examples will provide fluid transfer and resist internal rotation, the configurations in FIGS. 6A, 6C, 6E and 6F will provide the optimal rigidity and flexibility.

To provide an optimal combination of fluid transfer, comfort, rigidity and flex, the range of dimensions for the OD outer catheter 105A-G and OD of the inner catheter 110A-G are narrow. The preferable OD of the outer catheter 105A-G is about 4 mm and the OD of the inner catheter 112A-G in the range of about 1.5 mm to 2 mm with R1 being about 2-2.5 mm.

Figure 7:
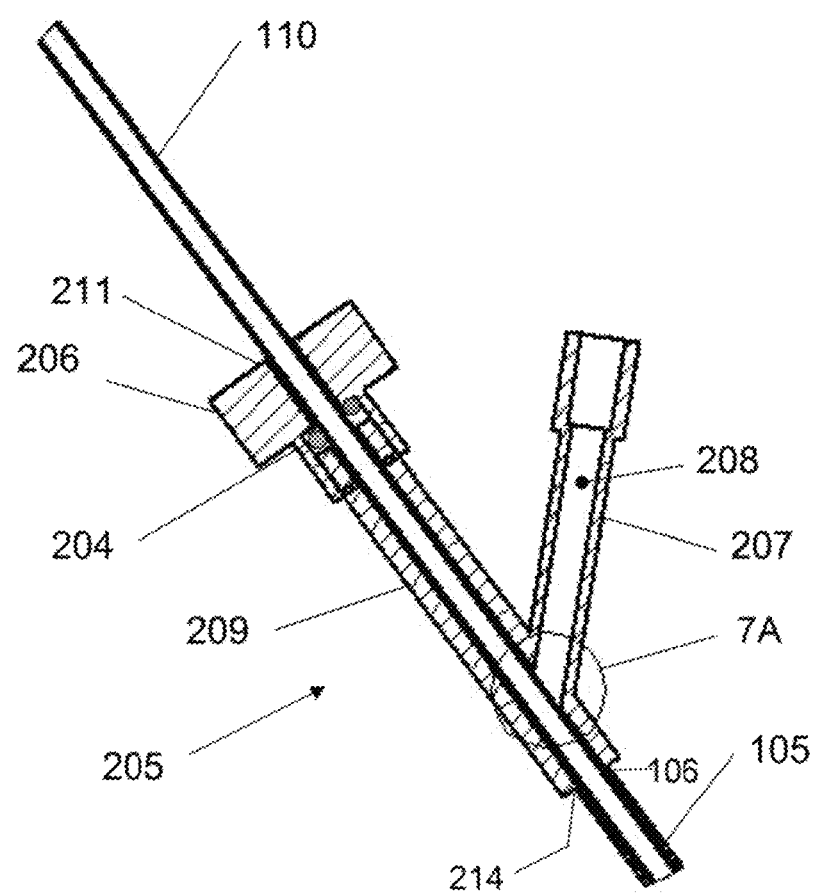
FIG. 7 is a cutaway view of the interior of the catheter showing the dimensioning between the inner catheter and the interior channel of the Y connector.

These dimensions permit the required fluid transfer of the 1.5 cu. mm to evert the balloon per 1 mm length required, It should be noted that the disclosed catheter system 100 does not utilize a guide wire as with prior art devices such as the guide wire 76 of the Hall U.S. Pat. No. 4,946,440. Normally the guide wire would provide the rigidity during insertion, however in the disclosed device the rigidity is provided by the configuration of the inner catheter 110A-G and outer catheter 105AG. FIG. 7 shows a cross section of the Y connector 205, with the inner catheter 110 passing through the straight arm of the piece that contains the gasket 204 which seals off the interior space around the inner catheter 110, from the outside environment when the cap 206 is tightened on the body 209 of the Y connector 205. In addition the cap 206 holds the inner catheter 110 in place and prevents accidental movement relative to the Y-connector 205. The inflation syringe 220, which is not shown in this figure, attaches to the sidearm 207. The sidearm 207 has an interior channel 208 that communicates to the interior channel 107 to provide passage to the balloon interior 122. The proximal end 106 of the outer catheter 105 is bonded to the distal end 214 of the Y connector 205 and seals the inflation space 107 from the outside environment.

Figure 8:
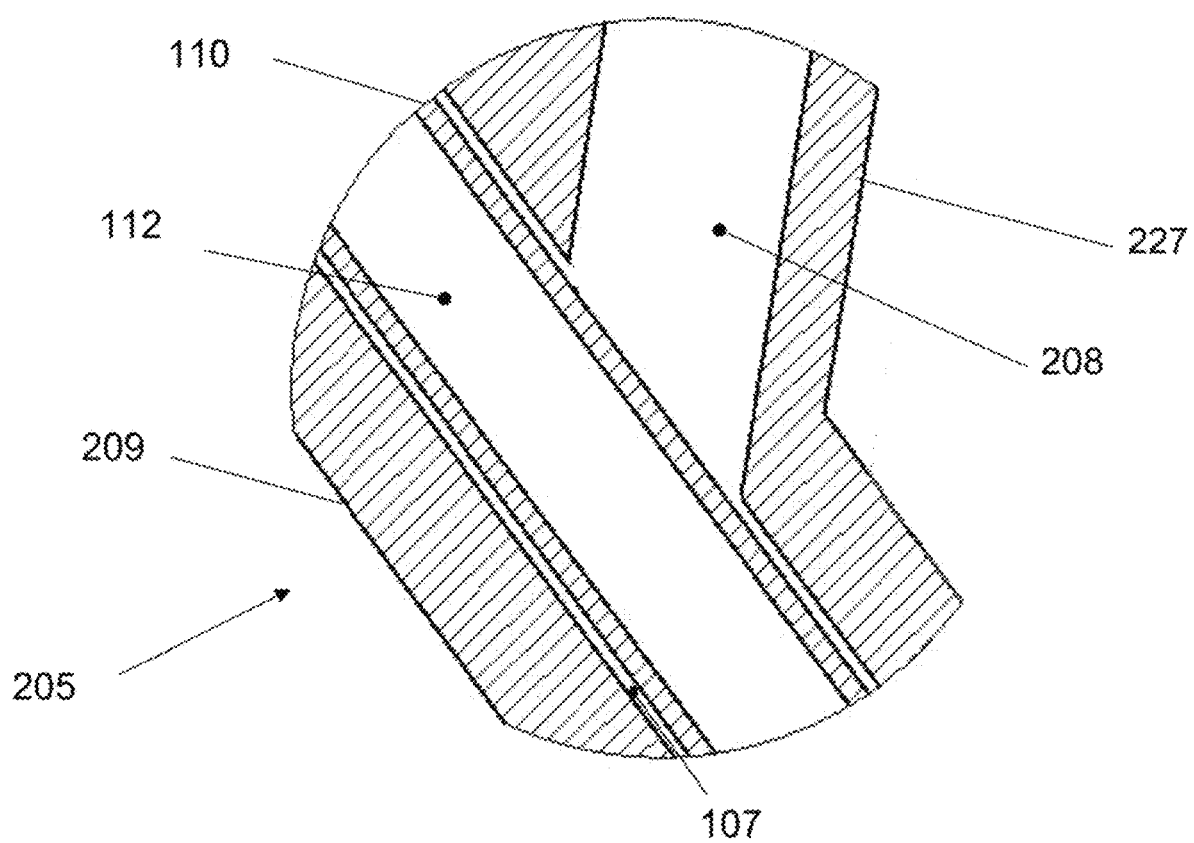
FIG. 8 illustrates the magnified area of the junction between the side arm and the main body of the Y connector.

FIG. 8 shows the magnified area of the junction between the side arm 207 and the main body 209 of the Y connector 205, defined in FIG. 7 by section 7A. The inner catheter 110 has a smaller outer diameter than the interior channel of the Y connector, 205. The inflation syringe 220 attaches to sidearm 207 and the inflation space 208 is uninterrupted and extends into the interior space 107 around the inner catheter 110. This enlargement is to clarify the association of the inflation space 107 and the inner catheter 110 within the Y connector 205. At the distal end of the Y connector 205 the inflation space 107 exists between the outer catheter 105 and the inner catheter 110.

Figure 9:
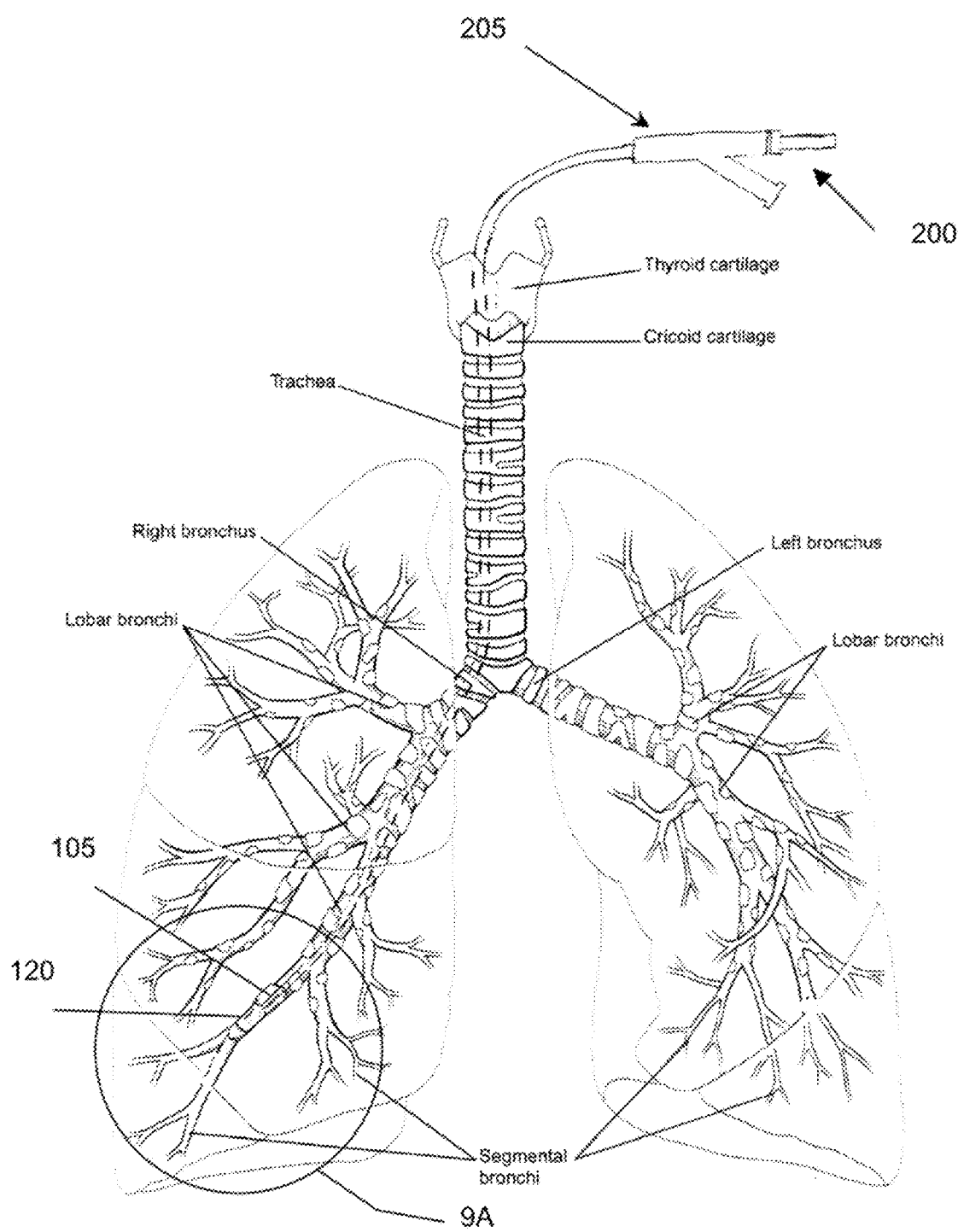
FIG. 9 is a schematic representation to show the balloon wedged in the bronchi of the lung.

FIG. 9 is a schematic representation of the catheter 100 in its primary usage where it would be inserted through the mouth and guided down the trachea into the bronchial tree into a lobe of the lung to a level of the Lobar bronchi. Once the catheter is too large to fit any further, the operator slightly withdraws the device 100 a slight amount and then advances the inner catheter 110 the pre-determined distance BL to deploy the balloon 120. The balloon 120 is inflated using the syringe 220 and the high-volume low-pressure material (air) effectively seals off the sampling region from any contamination. Once the balloon 120 is in place, the sampling fluid is injected through the lumen of the sampling catheter 130 that has been passed down through inner catheter 110 until it transverses the length of the device 100' and exits the distal end 117 to fill the segmental bronchi with sterile fluid. The fluid would be suctioned from the lower bronchioles and alveoli using a syringe attached to the sampling catheter and the collected fluid processed for any pathogens in the lung.

Figure 10:
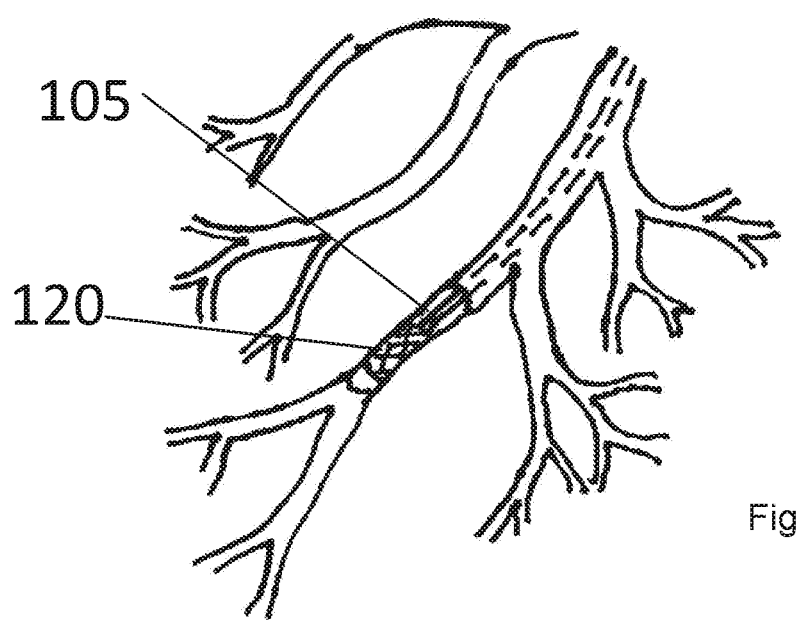
FIG. 10 is a schematic representation of area 9A in FIG. 9 to show the balloon wedged in the bronchi of the lung.

FIG. 10 is a schematic representation of area 9A in FIG. 9 to show the balloon 120 wedged in the bronchi of the lung.

Description of the Usage of the Invention

The wedging of the bronchoscope is simulated in one object of the current invention by incorporating an inflatable high-volume, low-pressure polyurethane balloon 120 into the catheter system. The balloon lumen 120 is contained between the inner 110 and outer 105 catheter members, with the polyurethane balloon 120 attached to the exterior of the outer 105 and inner 110 catheters. When in the retracted position, the balloon material 120 folds into the lumen 112 between the catheters, forming a seal around the distal opening of the inner catheter 110. This maintains the pristine environment of the inner lumen 112 of the catheter member 110, as the device is advanced into the pulmonary track, and ensures that the collected sample is representative of the lower bronchioles and alveoli not of secretion or drippings from the trachea and bronchi.

When the device 100 reaches the target sampling region as shown in FIG. 9, the user advances the inner catheter member 110 a pre-determined distance BL to deploy the balloon. The cap 206 seals and locks the inner catheter 110 to the Y-connector 205. Air or a sterile fluid is introduced through the balloon lumen and inflates the balloon until it seals the bronchiole, effectively isolating the target area from upper airway contamination. The incorporation of the high-volume, low-pressure balloon eliminates the risk of damage the bronchioles and alveoli posed by the forced wedging of the rigid bronchoscope. The balloon can expand to seal the lower pulmonary track even in the event of a non-circular bronchiole cross-section. The sampling device transverses the length of the catheter and emerges through the unblocked opening of the inner catheter. If multiple passes are needed to collect the proper amount of cytological material, sampling device can be removed from the catheter assembly and replaced with a new sampling device without removing or disengaging the balloon.

To maintain proper alignment of the balloon and restrict torsion or tearing, the two catheters must not rotate with respect to one another. Maintaining the proper configuration can be achieved by utilizing tubing in which the interior configuration of the outer tubing is non circular but complimentary to the outer configuration of the inner tubing thus allowing axial motion but not rotational motion relative to one another. In one embodiment, the inner and outer tubes can be made using tubing of various shapes to minimize rotation of the inner tube relative to the outer tube when deploying and retracting the balloon. The complimentary shapes between the inner and outer catheters should be at least at the distal end near the balloon.

The novel catheter system 100 disclosed utilizes a primary catheter shaft 105 provided with multiple lumen or passageways extending the length thereof. A microbiological sampling device for obtaining contamination-free specimens is comprised of an outer catheter 105 and an inner catheter 110, each having a distal end and a proximal end. FIGS. 1A and 1B show the device in both the retracted 100, and deployed 100' configuration, respectively, to illuminate the connection between the distance the specialized holder stop 210 moves and the length of the balloon 120. When the device is in place and ready for balloon 120 deployment, the user advances the inner catheter 110 relative to the outer catheter 105 until the holder stop 210 reaches the proximal face 211 of the Y connector 205. This displacement everts the balloon 120 to its full length, BL. Once the balloon 120 is everted, the inflation syringe 220 is attached to the Y connector 205 and fluid (air) is introduced to inflate the balloon 120.

The inner tube, 110, passes through the gasket 204, FIG. 7 at the proximal end screw cap 206 of the Y-connector 205 to from an air tight seal. When the device 100 is in use, the gasket 204 of the Y-connector 205 is closed around the inner tube 110, to seal the space between the inner catheter 110 and the outer catheter 105. The distal tip 117 (FIG. 4) of the inner catheter 110 is retracted within the outer catheter 105. The proximal end 106 of the outer catheter 105 is securely bonded to the distal end 214 of the Y-connector 205 and creates a sealed cavity 227 between the inner catheter 110 and outer catheter 105. Area 7A is illustrated in more detail in FIG. 8. As previously illustrated, the catheter 110 is secured by the handle 200 and the distance BL established by the holder stop 210. The remainder of the assembly screws into the handle component and further stabilizes the movement of the inner catheter 110. The proximal inner catheter handle 200 includes a silicone or other suitable material gasket to hold the inner catheter 110. When the device is deployed and in place, a sampling tube can be passed through the inner catheter 110.

The interior catheter 110, having an outer diameter smaller than the inner diameter of the outer catheter 105, as well as a configuration that will not rotate, moves axially with respect to the outer catheter 105. The outer diameter of the inner catheter 110 is typically non-circular and complimentary to the non-circular inner diameter of the outer catheter 105. The spacing between the outer diameter of the inner catheter 110 and the inner diameter of the outer catheter 105 is such that the inner catheter 110 cannot rotate more than 45 degrees, and preferably about 15 degrees, relative to the outer catheter 105. The rotation range can be between about 2 degrees and about 45 degrees and is preferably between about 5 degrees and about 15 degrees. The prevention of rotation of the inner catheter 110 relative to the outer catheter 105 prevents the balloon 120 from being twisted which can result in the balloon 120 from not everting or inflating. The inner diameter of the interior catheter 110 must be sufficient to permit a sampling device 130 to easily transverse the inner catheter 110 length. As described in detail in FIGS. 6A-6G, the outer surface of the inner catheter 110 has an outer surface, either whole or partially, configured, in relationship to the inner surface of the outer catheter 105, to prevent rotation of one catheter relative to the other. At the distal end of the catheter assembly 100 is attached a balloon 120. Preferably the balloon 120 is attached to the outer surface of the primary catheter 105 and the outer surface of the inner catheter 110. When the device 100 is in the retracted position, the inner catheter member 110 terminates slightly short of the distal end of the primary outer catheter 105, FIG. 2. In this condition the pair of catheters can be advanced through the upper respiratory system of the patient without contaminating the inner catheter as the retraced balloon prevents fluid from entering the channel of the inner catheter. Once the device transverses the pulmonary track and reaches the sampling region, the proximal end of the inner catheter is advanced to the predetermined distance set by means of the handle, FIG. 9. The catheter handle 200 holder stop 210 limits the longitudinal separation between the retracted and deployed positions to a predetermined maximum distance BL. As the inner tube 110 is extended axially relative to the outer catheter 105, the distal portion of the inner support member extends outside the catheter body and straightens out the balloon component.

It should be noted that the configuration of the catheter as illustrated herein is one type of catheter that would benefit from the disclosed catheter tube configurations and holder stop. Other existing or future catheter designs that use inner and outer tubes will benefit from the novel designs disclosed herein.

LIST OF COMPONENTS

100 Device in retracted position
100' Device in deployed position
105 outer tube
107 annular space/channel between inner and outer tubing
108 notch on inner surface of outer tube
109 protrusion
110 inner catheter
112 space within tube 110
116 distal end tube 105

117 distal end of tube 110
120 Balloon
122 balloon space
130 sampling tube
200 inner catheter handle
204 sealing gasket
205 Y connector
206 screw cap
207 side arm of Y connector
208 interior channel of side arm 207
209 main body of the Y connector
210 handle on assembly 200
211 proximal end screw cap
220 inflation syringe
BL balloon length and handle travel

What is claimed is:

1. A diagnostic catheter system for introduction into a body cavity comprising:
   i. a handle, said handle comprising:
      a. a proximal face;
      b. a distal face;
      c. a handle stop; and
      d. a receiving area extending from the proximal face to the handle stop and dimensioned to receive a flexible inner tube;
   ii. a Y connector comprising:
      a. a proximal face, said proximal face being configured to prevent said handle stop from further movement;
      b. a distal face;
      c. a tube receiving channel between the proximal face and the distal face; and
      d. a port for introducing a fluid under pressure into the catheter system;
   iii. a flexible outer tube comprising:
      a. an exterior periphery having a first cross-section and a first dimension;
      b. an interior periphery having at least one second non-circular cross-section and a second dimension less than the first dimension;
      c. a distal end adapted for insertion into the body cavity; and
      d. a proximal end connected to the distal face of the Y connector;
   iv. a flexible inner tube dimensioned to be received within the flexible outer tube, said flexible inner tube comprising:
      a. an exterior periphery having at least one third non-circular cross-section and a third dimension less than the second dimension, wherein said at least one third non-circular cross-section of said inner tube is geometrically compatible with said at least one second non-circular cross-section of said flexible outer tube;
      b. an interior periphery having a fourth cross-section and a fourth dimension less than the third dimension; and,
      c. an inner tube distal end adapted for insertion into the body cavity;
   v. an expandable membrane coupled to the distal end of the flexible outer tube and the inner tube distal end; and
   vi. an annular space to enable a fluid transfer volume via said port to inflate said membrane, said annular space formed by the flexible outer tube second dimension and the flexible inner tube third dimension when said flexible inner tube is positioned within said flexible outer tube;
wherein the at least one third cross-section of said flexible inner tube and the at least one second cross-section of said flexible outer tube engage in a longitudinally slidable alignment configured to prevent more than a predetermined rotation and to provide support for said flexible inner tube and flexible outer tube without a guidewire; and
wherein when the handle is in a retracted position, the handle stop is distanced from the proximal face of the Y connector a distance equal to the everted length of the membrane; and
wherein when the handle is in a deployed position, the handle stop contacts the proximal face of the Y connector to inhibit over deployment of the membrane by preventing insertion of the flexible inner tube into the flexible outer tube beyond the everted length of the membrane, the distance between the retracted position and deployed position being the membrane deployment.

2. The catheter system of claim 1 wherein said second cross-section and said third cross-section are the same polygon.

3. The catheter system of claim 1 wherein the fluid transfer volume in the annular space is 1.5 cu. mm per 1 mm length.

4. The catheter system of claim 1 wherein the membrane deployment is between 5 mm and 10 mm.

5. The catheter system of claim 1 further comprising at least one protrusion extending from the exterior periphery of the flexible inner tube and at least one notch within said interior periphery of the flexible outer tube wherein locating said at least one protrusion within said at least one notch prevents the flexible inner tube and the flexible outer tube from rotating relative to one another.

6. The catheter system of claim 1 further comprising at least one protrusion extending from said interior periphery of the flexible outer tube and at least one notch within said exterior periphery of the flexible inner tube wherein locating said at least one protrusion within said at least one notch prevents the flexible inner tube and the flexible outer tube from rotating relative to one another.

7. The catheter system of claim 1 wherein the predetermined rotation is between 5 degrees and 15 degrees.

8. The catheter system of claim 1 wherein said predetermined rotation is between 2 degrees and 20 degrees.

9. The catheter system of claim 1 wherein the fluid transfer volume is 1.5 cubic mm per 1 mm of tube length.

10. The catheter system of claim 1 wherein the membrane has a fluid capacity of 100 cu mm to 1000 cu mm.

11. The catheter system of claim 1 wherein the flexible outer tube has an outer diameter of 4 mm and the flexible inner tube has an outer diameter of 1.5 mm to 2 mm.

12. The catheter system of claim 1 wherein the at least one third cross section extends from the proximal end to the distal end of the flexible inner tube and the at least one second cross section extends from the proximal end to the distal end of the flexible outer tube.

13. The catheter system of claim 1 wherein the at least one third cross section is at the distal end of the flexible inner tube and the at least one second cross section is at the distal end of the flexible outer tube.

14. A tubular system having an annular space for fluid transfer along the length comprising:
   i) a flexible outer tube comprising:
      an exterior periphery having a first cross-section and a first dimension;
      an interior periphery having at least one second non-circular cross-section and a second dimension less than said first dimension; and ii) a flexible inner tube comprising:
an exterior periphery having at least one third non-circular cross-section and a third dimension less than the second dimension; and
an interior periphery having a fourth cross-section and a fourth dimension less than the third dimension;
wherein the flexible outer tube second dimension and the flexible inner tube third dimension form an annular space to enable a fluid transfer volume of 1.5 cubic mm per 1 mm of tube length; and
wherein the at least one third cross-section of the flexible inner tube and the at least one second cross-section of said flexible outer tube engage in a longitudinally slidable alignment configured to limit rotation between 2 degrees and a maximum rotation of 45 degrees and to provide support for said flexible inner tube and flexible outer tube without a guidewire.

15. The tubular system of claim 14 wherein the flexible outer tube has an outer diameter of 4 mm and the flexible inner tube has an outer diameter of 1.5 mm to 2 mm.

16. A catheter for introduction into a body cavity including a flexible outer tube and a flexible inner tube substantially co-axial therewith and slidable within the flexible outer tube to define an annular channel there between,
the flexible outer tube comprising:
an exterior periphery;
an interior periphery;
a distal end;
a proximal end; and
the flexible inner tube comprising:
a distal end,
a proximal end, and
an exterior periphery having a radius less than said interior periphery of the outer flexible tube to permit fluid from a port within a Y connector to inflate a membrane;
wherein, a cylindrical membrane coupled to both the distal end of the flexible outer tube and the distal end of the flexible inner tube, defines a pristine chamber when the membrane is in a first, reflected position within the flexible outer tube; and
wherein, a holder member, having a tube receiving area extending from a holder distal end to a holder proximal end is dimensioned to receive the flexible inner tube, and
wherein improvements comprise:
the exterior periphery of the flexible outer tube having a first cross-section and a first dimension;
the interior periphery of the flexible outer tube having a second non-circular cross-section and a second dimension less than the first dimension; and
the flexible inner tube dimensioned to be received within the tube receiving area and within the interior periphery of the flexible outer tube and comprising:
an exterior periphery having a third non-circular cross-section and a third dimension less than the second dimension; and
an interior periphery having a fourth cross-section and a fourth dimension less than the third dimension;
wherein the third cross-section of the exterior periphery of the flexible inner tube prevents more than a 20% rotation within the second cross-section of the interior periphery of the flexible outer tube, spacing between the second cross-section and the third cross-section creating the annular channel for a fluid transfer volume of 1.5 cubic mm per 1 mm of tube length, and
wherein when the holder member is in a retracted position the distal end of the holder member is distanced from a proximal face of the Y connector 5 mm to 10 mm, a distance equal to an everted length of the membrane and when the holder member is in a deployed position the distal end contacts the proximal face of the Y connector to prevent insertion of the flexible inner tube into the flexible outer tube beyond the everted length of the membrane, the configuration of the second cross-section and the third cross-section preventing rotation during insertion of the catheter, providing support of said flexible inner tube and flexible outer tube without a guidewire, and providing the annular channel to enable the fluid transfer volume for full deployment of the membrane.

17. The catheter of claim 16 wherein said rotation is between 2 and 45 degrees.

18. The catheter of claim 16 wherein said predetermined rotation is between 5 and 15 degrees.

19. The catheter of claim 16 wherein the flexible outer tube has an outer diameter of 4 mm and the flexible inner tube has an outer diameter of 1.5 mm to 2 mm.

20. The catheter system of claim 16 wherein the membrane has a fluid capacity of 100 cu mm to 1000 cu mm.

* * * * *